(12) United States Patent
Manku et al.

(10) Patent No.: US 7,319,147 B2
(45) Date of Patent: Jan. 15, 2008

(54) PORPHYRINS AND RELATED COMPOUNDS

(75) Inventors: Mehar Manku, NR Carlisle (GB); David C Rice, Edinburgh (GB)

(73) Assignee: Bioscience Technology Investment Holdings Limited, Labuan (MY)

( * ) Notice: Subject to any disclaimer, the term of this patent is extended or adjusted under 35 U.S.C. 154(b) by 179 days.

(21) Appl. No.: 10/363,909

(22) PCT Filed: Jan. 22, 2001

(86) PCT No.: PCT/GB01/00236

§ 371 (c)(1),
(2), (4) Date: May 12, 2005

(87) PCT Pub. No.: WO01/53300

PCT Pub. Date: Jul. 26, 2001

(65) Prior Publication Data

US 2006/0040913 A1 Feb. 23, 2006

(30) Foreign Application Priority Data

Jan. 21, 2000 (GB) .................................. 0001455.5

(51) Int. Cl.
*C07B 47/00* (2006.01)
*C07D 487/22* (2006.01)

(52) U.S. Cl. ..................................................... 540/145

(58) Field of Classification Search ................ 540/145; 534/15; 514/185, 410
See application file for complete search history.

(56) References Cited

FOREIGN PATENT DOCUMENTS

| EP | 0186962 | * | 11/1985 |
| EP | 0 186 962 | | 7/1986 |
| EP | 0 186 962 A1 | | 7/1986 |
| EP | 0337601 A1 | * | 2/1989 |
| EP | 0 337 601 A1 | | 10/1989 |

OTHER PUBLICATIONS

Szterenberg et al, "Structure and Stability of 2-Aza-21-carbaporphyrin Tautomers Prearranged for Coordination", Inorg. Chem., vol. 36, 1997, pp. 6287-6291.
Furuta et al, "N-Confused Tetraphenylporphyrin-silver(III) Complex", Inorg. Chem, vol. 38, 1999, pp. 2676-2682.
Szterenberg et al, "Structure and Stability of 2-Aza-21-carbaporphyrin Tautomers Prearranged for Coordination", Inorg. Chem. 1997, 36, 6287-6291; XP-001000335.
Furuta et al, "N-Confused Tetraphenylporphyrin-Silver (III) Complex[1]", Inorg. Chem. 1999, 38, 2676-2682; XP-001000333.
Sternberg et al, "Porphyrin-based Photosensitizers for Use in Photodynamic Therapy", Tetrahedron 54 (1998) 4151-4202.
Furuta et al, "N-Fused-Porphyrin": A New Tetrapyrrolic Porphyrinoid with a Fused Tri-pentacyclic Ring, J. Am. Chem. Soc. (2000), 122(24), 5748-5757.

* cited by examiner

Primary Examiner—James O. Wilson
Assistant Examiner—Paul V. Ward
(74) Attorney, Agent, or Firm—Nixon & Vanderhye

(57) ABSTRACT

New porphyrins and chlorins including bacteriochlorins, for photodynamic therapy.

8 Claims, No Drawings

PORPHYRINS AND RELATED COMPOUNDS

FIELD

The invention relates to porphyrins and chlorins for photodynamic therapy, of cancerous and other diseased tissues.

BACKGROUND

Certain N-confused porphyrins have been known since 1994 (E. D. Steinberg et al, Tetrahedron 1998, 54, 4151-4202, see 4192 and 4193 specifically). They are of a structure that may be represented, when substituted with phenyl rings at the meso positions as herein proposed, as shown in Figure I.

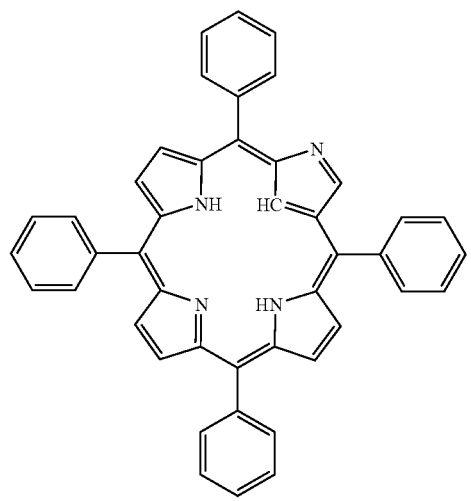

Recently, Lindsey et al have published a ready synthesis of such N-confused porphyrins (G. R. Geier, D. M. Haynes, J. S. Lindsey, Organic Letters 1999, 1(9), 1455-1458).

Also known, in our European Patent Specifications Nos. 0186962 and 0337601 are tetrahydroxyphenyl derivatives of porphyrins, chlorins and bacteriochlorins, for photodynamic therapy (PDT) of cancerous tissue. These compounds have good properties and, among them, tetra(3-hydroxyphenyl) dihydroporphyrin or m-THPC is well into the stages of product development for PDT. Nevertheless, improvements in PDT compounds in respect of absorption wavelength and hence depths of PDT necrosis, tissue selectivity, water-compatibility, and ease of synthesis are sought. PDT compounds also have application as light activated agents with the power to kill viruses and bacteria that are now proving resistant to conventional antibiotics.

THE INVENTION

We propose the following N-confused tetrahydroxyphenyl and tetra-alkoxyphenyl porphyrins represented as Figures IIA and IIB, and the corresponding chlorins (dihydroporphyrins) and bacteriochlorins (tetrahydroporphyrins), including tautomers in all cases, and their metallates and salts, including internal salts, as new compounds valuable in PDT.

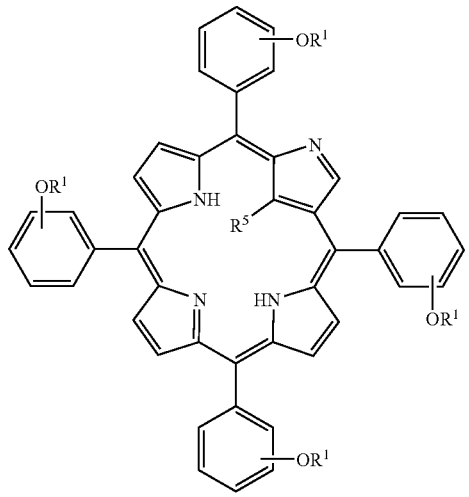

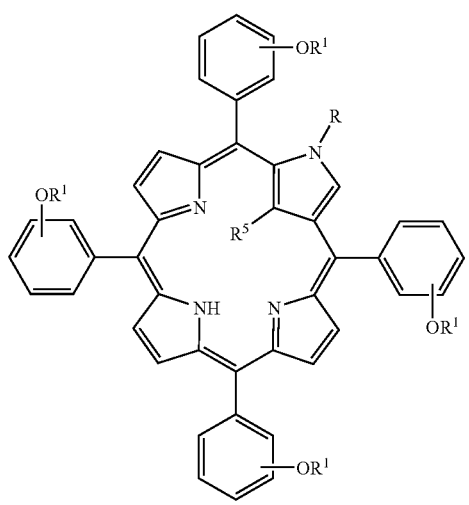

In formulae IIA and IIB, $OR^1$ stands for a hydroxy group ($R^1$=hydrogen) or an alkoxy group where $R^1$ is a branched or unbranched alkyl group containing from 1 to 4 carbon atoms; $OR^1$ may be at any position on the phenyl ring and there may be zero, one, two or three groups per phenyl ring provided at least one of the rings is substituted. A single m-hydroxy group on each phenyl ring is specifically suitable.

In formula IIB, examples of R (besides hydrogen where IIB and IIA represent tautomers of the same molecule) are:

R=X, a branched or unbranched alkyl group of 1 to 6 carbon atoms, or an aralkyl group the alkyl chain of which contains 1 to 3 carbon atoms.

R=XY where Y consists of 1 to 3 substituents which may be linked and/or attached to any of the carbons in X. Examples of Y are the following:

=—$SO_3H$, $CO_2H$ and their C1 to C12 esters and amides.
=—OH or $OR^2$ where $R^2$=a polyhydroxylated alkyl moiety from 1 to 20 carbon atoms, e.g. a carbohydrate, or derivatised amino acid such as a folic acid residue.
=—$NR^3R^4$ where $R^3$, $R^4$ are the same or different and may be hydrogen or an alkyl group of 1 to 12 carbon atoms or a polyhydroxylated alkyl chain or derivatised amino acid residue as last.

=Z-P where P is an end-capped polyalkylene preferably polyethylene glycol group of molecular weight of 2,000 to 100,000, preferably 5,000 to 40,000 and very preferably 10,000 to 20,000 Da and Z is a linker group to attach P e.g. the —(C═O)NH(CH$_2$)$_6$NH(C═O)O— group.

$R^5$=hydrogen, a halogen or a nitro group.

The invention also extends to the use of compounds as above in the preparation of a medicament for photodynamic therapy, in treatment of tumours or other disease, and such medicament and therapy itself.

The disclosed compounds are considered to be of use, for example, in the treatment of cancerous conditions such as, but not limited to, head and neck, liver, pancreatic and prostate cancers and other disease conditions such as, but not limited to, Barrett's Oesophagus, Age-related Macular Degeneration (ARMD), keratinoses, diabetic neuropathy, peripheral vascular disease, coronary artery disease, and other disorders arising from bacterial or viral infections.

STRUCTURES

In the above porphyrin formulae it will be recognised that when R=H, IIA and IIB are tautomeric forms and also that formally each represents a number of individual tautomers such as are shown below (all represented without the meso-phenyl groups and with $R^5$=H).

II.A.1

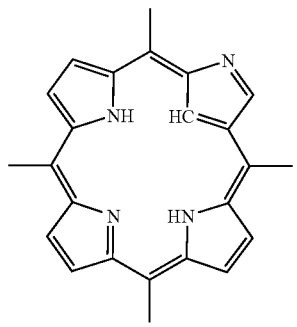

II.A.2

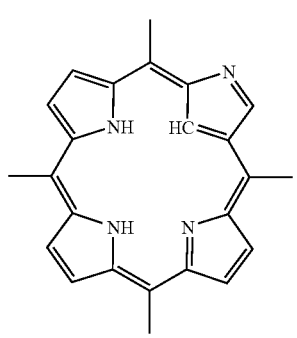

-continued

II.A.3

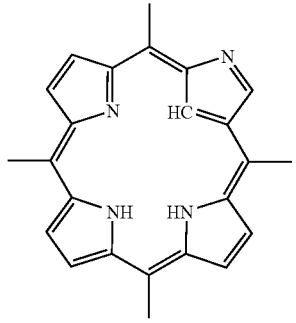

II.A.4

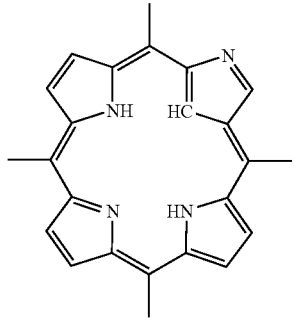

II.A.5

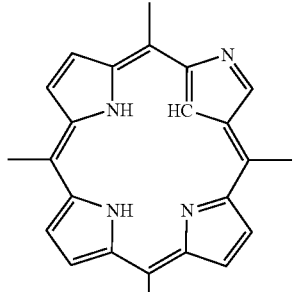

II.A.6

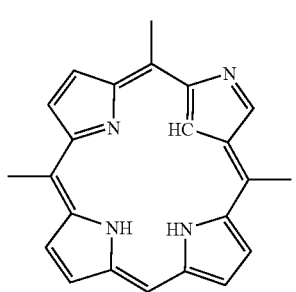

II.B.1

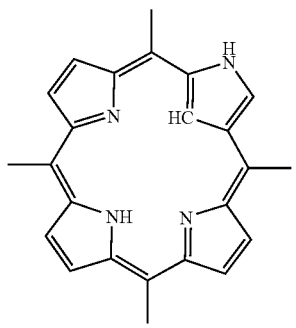

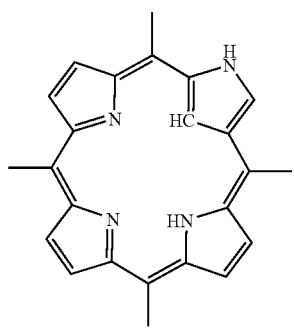
II.B.2
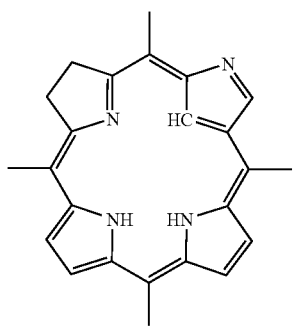
IIIC
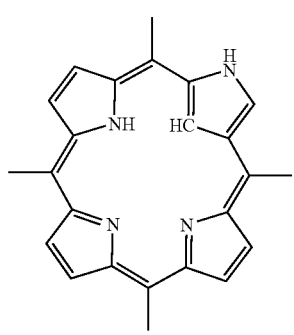
II.B.3
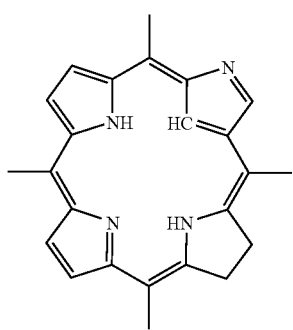
IIID
Corresponding chlorins to formula IIA may be represented by IIIA-D:
Corresponding chlorins to formula IIB may be represented by IVA-IVD:
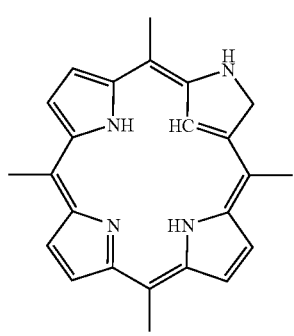
IIIA
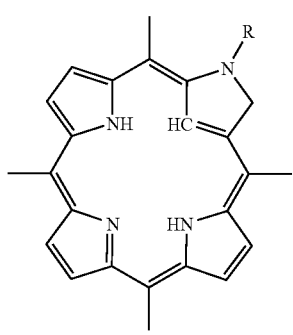
IVA
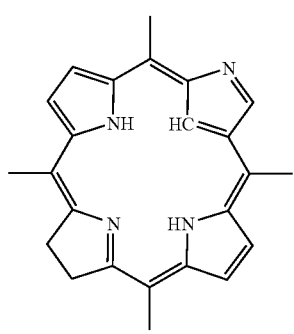
IIIB
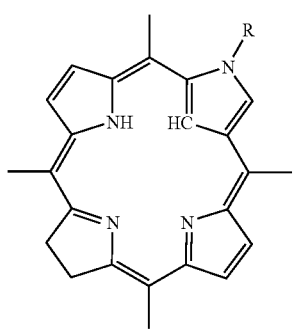
IVB

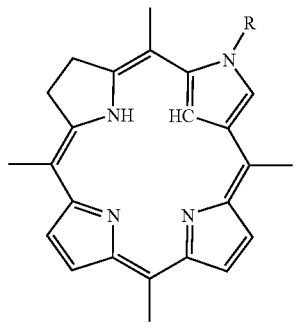 IVC
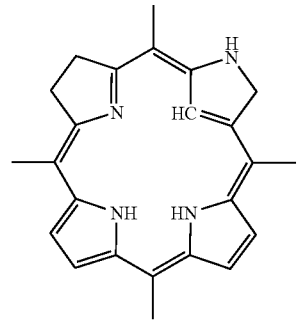 VC
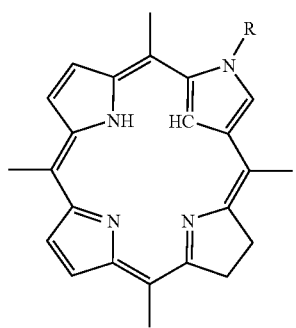 IVD
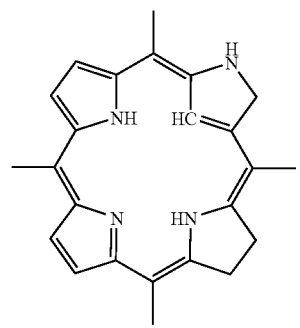 VD
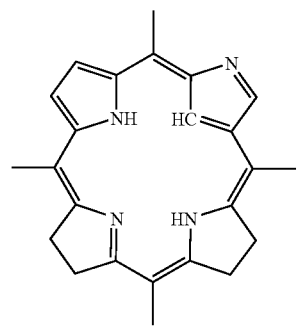 VE
Corresponding bacteriochlorins to formula IIA may be represented by VA-F:
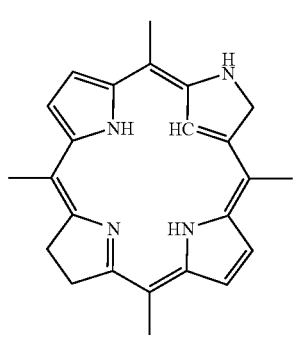 VA
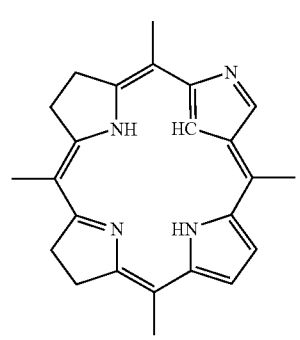 VF
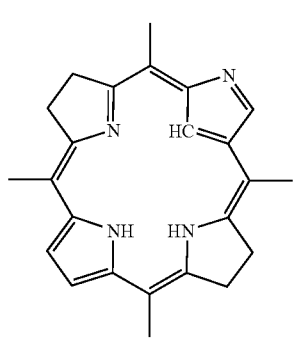 VB
Corresponding bacteriochlorins to formula IIB may be represented by VIA-F:

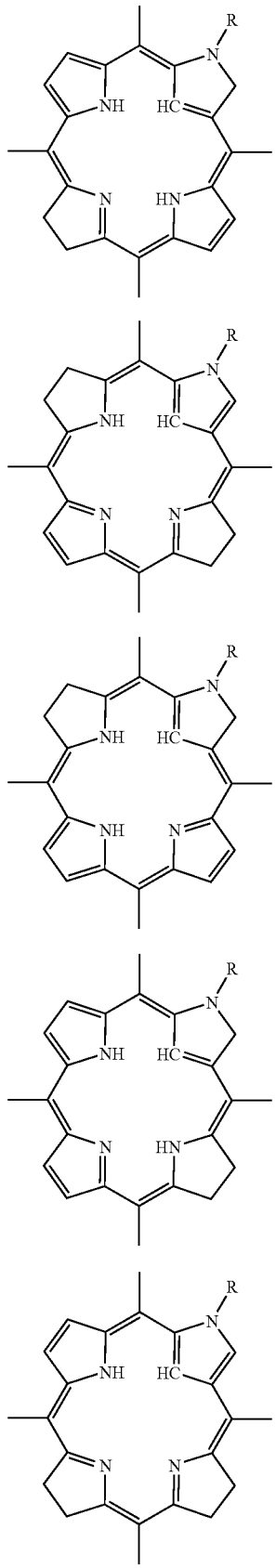

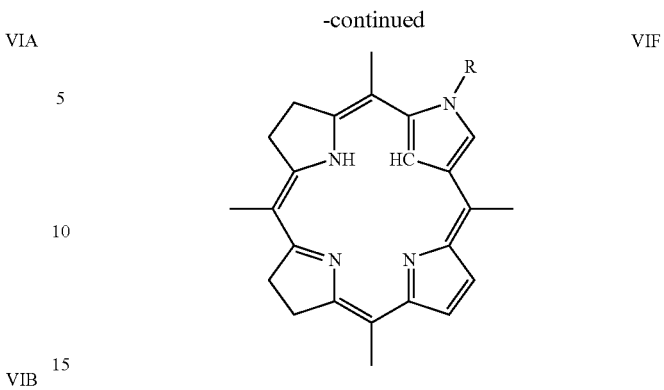

The invention covers all tautomers of the above compounds, and is not limited to those shown in the diagrams. There are no optical isomers.

DISCUSSION

As noted above, N-confused porphyrins (NCPs), or 2-aza-21-carbaporphyrins to give them a more correct IUPAC nomenclature, are a relatively new class of tetrapyrrolic macrocycles recently discovered as by-products from the routine preparation of the structurally isomeric meso-substituted porphyrins. They are unusual in that one of the macrocycle's pyrrole rings has been inverted so that what was once a central nitrogen atom has now become an external, quaternisable nitrogen, hence the term 'N-confused'. This nitrogen now has the potential for ready introduction of functionality into the molecule. Unusually, the now-central C—H bond is quite labile, allowing metallation of the macrocycle almost as easily as in the porphyrinic isomers (See Figure VII, P. J. Chmielewski et al, J. Chem. Soc. Perkin Trans. 2, 1995, 503-509).

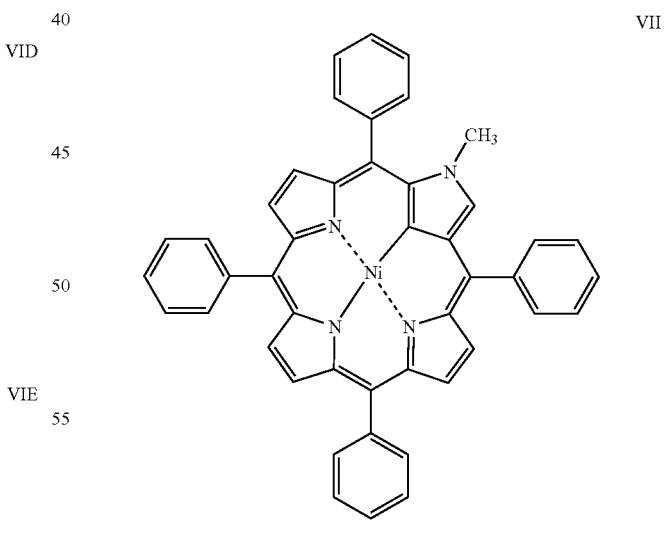

Until very recently, the N-confused porphyrins have remained a laboratory curiosity mainly due to the low yields of these compounds. However, authors have remarked on the potential of N-confused porphyrins in the PDT field because of their significantly different UV/Visible spectra when compared to porphyrins. Thus, the reduction in symmetry, and hence perturbation of the pi-electronic structure, caused by N-confusion, leads to significant red-shifting and increased intensity of the lowest energy Q band compared to the corresponding porphyrins. The intensity of this low energy band can be further increased by quaternisation of the external nitrogen. It is also noted that the UV/Visible spectrum is pH dependent.

With the publication by Lindsey of a synthetic route producing relatively high yields of meso substituted N-confused porphyrins, these unusual compounds were opened up for research. For example, though the compounds have been known since 1994 and some studies on coordination properties and reactivity have been reported, photophysical studies had not been performed to ascertain potential as PDT agents.

In initial experiments, 2-aza-21-carba-5,10,15,20-tetraphenylporphyrin, was synthesised by the method of Lindsey and subsequent reaction with methyl iodide at room temperature led to conversion of the N-confused porphyrin to an N-methyl derivative with a lowest energy Q-band to B-band intensity ratio similar to m-THPC. No reduction to the N-confused chlorin was necessary to achieve these comparable intensity ratios. This reaction was duly performed on the tetrahydroxyphenylporphyrin derivative, with similar results (See Scheme 1).

EXAMPLES

The following patent examples are given and are summarised in the intervening schemes shown below. The synthesis of the N-methyl substituted N-confused porphyrin depicted in Scheme 1 is outlined in examples 1-5.

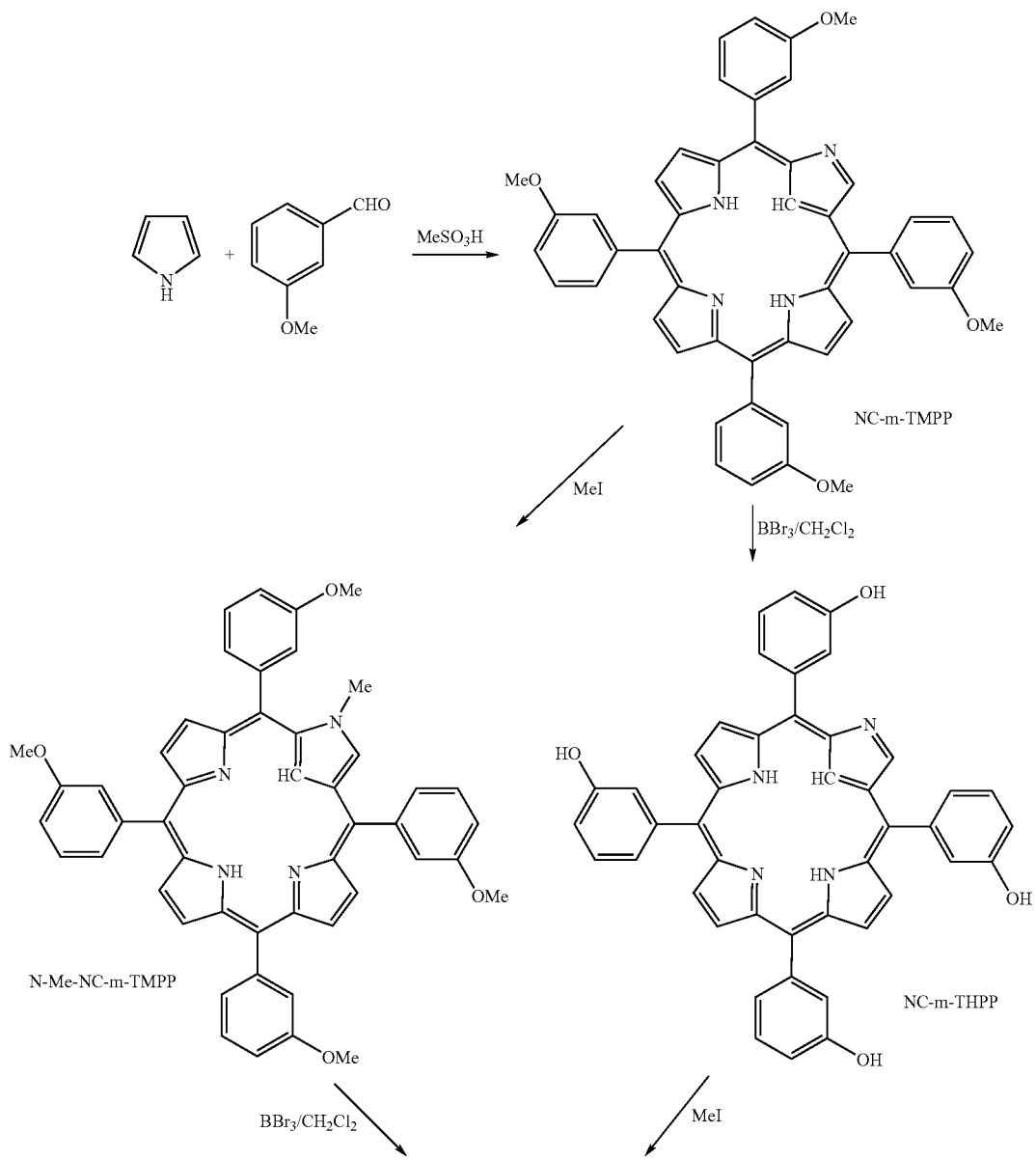

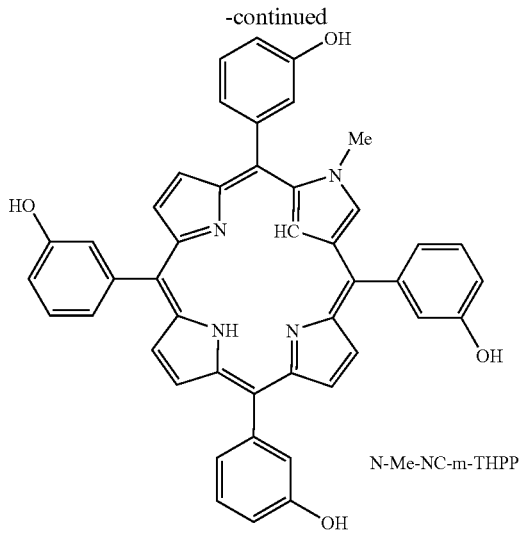

N-Me-NC-m-THPP

Example 1

2-Aza-21-carba-5,10,15,20tetra(3-methoxyphenyl)porphyrin (NC-m-TMPP)

Pyrrole (1.04 ml, 15 mmol) and 3-methoxybenzaldehyde (1.82 ml, 15 mmol) were mixed with methanesulfonic acid (0.68 ml, 10.5 mmol) in a large volume of dichloromethane (1500 ml) at room temperature (RT). The reactants were allowed to stir for 30 min and then the reaction was terminated by the addition of 2,3-dichloro-5,6-dicyano-1,4-benzoquinone (3 g, 13.2 mmol). After stirring for 1 min, triethylamine (5.8 ml) was added to neutralise the solution and the resultant mixture left to stir for a further 10 min. Initial purification was achieved by passing the whole crude mixture through a column (60 mm) of basic alumina (300 g, activity III). Everything was collected as a single fraction, evaporated in vacuo to near dryness before being absorbed onto 15-20 g of basic alumina (activity III). This was added to the top of a column (50 mm) of basic alumina (300 g, activity III) eluting with 3:1 hexane/dichloromethane. The polarity of the eluant was increased from 3:1 to 1:1, to 1:3, and finally 100% dichloromethane. The porphyrin eluted first, with the desired N-confused porphyrin (NC-m-TMPP) eluting largely with 100% dichloromethane, and evaporated in vacuo to dryness. The product obtained was then refluxed with methanol (21 ml) for 10 min and then allowed to cool in the fridge for 2 h. After filtration the solid was washed with methanol (5 ml) and dried in a vacuum oven (60° C.) for 2 h to give the title compound as a micro-crystalline solid (780 mg, 28%). The porphyrin (m-TMPP) was obtained as a minor product (105 mg, 3.8%).

Increasing the pyrrole concentration to 11.5 mmol or 12.4 mmol and the other reactants accordingly led to a decreased yield of 24%. A modified procedure at lower dilution (equivalent to 20 mM) also resulted in a poorer yield of crystallised product (see below).

To a mixture of pyrrole (2.8 ml, 40 mmol) and 3-methoxybenzaldehyde (4.9 ml, 40 mmol) in dichloromethane (2000 ml) was added at RT with vigorous stirring methanesulfonic acid (2.6 ml, 40 mmol). The reactants were allowed to stir for 8 min after which the reaction was terminated by the addition of 2,3-dichloro-5,6-dicyano-1,4-benzoquinone (8 g, 35.2 mmol). After stirring for 1 min, triethylamine (16 ml) was added to neutralise the solution and the resultant mixture left to stir for a further 10 min. Initial purification was achieved by passing the whole crude mixture through a column (60 mm) of basic alumina (400 g, activity III). Everything was collected as a single fraction, evaporated in vacuo to 100 ml before being absorbed onto 50-60 g of basic alumina (activity III). This was added to the top of a column (60 mm) of basic alumina (600 g, activity III) eluting with 3:1 hexane/dichloromethane. The polarity of the eluant was increased from 3:1 to 1:1, to 1:3, and finally 100% dichloromethane. The porphyrin eluted first, with the desired N-confused porphyrin (NC-m-TMPP) eluting largely with 100% dichloromethane, and evaporated in vacuo to dryness. The product obtained was then refluxed with methanol (30 ml) for 10 min and then allowed to cool in the fridge for 2 h. After filtration the solid collected was washed with methanol (10 ml) and then dried in a vacuum oven (60° C.) for 2 h to give the title compound as a micro-crystalline solid (1.6 g, 22%).

NC-m-TMPP Physical Data: $\delta_H$ (360 MHz, CDCl$_3$) −5.01 (1H, s, H-21), −2.43 (2H, bs, NH), 3.99 (6H, s, OCH$_3$), 4.04 (3H, s, OCH$_3$), 4.19 (3H, s, OCH$_3$), 7.30-7.36 (4H, m, CH$_{ar}$), 7.61-7.78 (8H, m, CH$_{ar}$), 7.88-7.97 (4H, m, CH$_{ar}$), 8.59-8.66 (4H, m, H-8, 12, 13, 17), 8.81 (1H, s, H-3), 8.95 (1H, d, $J_{18, 17}$ 4.8 Hz, H-18), 9.02 (1H, d, $J_{7, 8}$ 4.9 Hz, H-7); $\lambda_{max}$ (CH$_2$Cl$_2$): 280 ($\epsilon$ 23 009), 441 ($\epsilon$ 19 8126), 540 ($\epsilon$ 10 858), 582 ($\epsilon$ 12 724), 725 ($\epsilon$ 11 930); m/z (+ve FAB, NOBA) 735 (MH$^+$, 9.9%), (Found: MH$^+$ 735.29711. C$_{48}$H$_{39}$N$_4$O$_4$ requires 735.29713).

Example 2

2-Aza-21-carba-5,10,15,20-tetra(3-hydroxyphenyl)porphyrin (NC-m-THPP)

NC-m-TMPP (200 mg, 0.27 mmol) was dissolved in dry dichloromethane (15 ml) and the solution was cooled to an external temperature of −78° C. A 1.0M solution of boron tribromide in dichloromethane (2.5 ml, 2.5 mmol) was added dropwise and the resultant reaction mixture stirred at −78° C. for 2 h. This was then allowed to warm up slowly to RT with continued stirring overnight. Next day, the mixture was cooled to an external temperature of −10° C.

and excess methanol (3 ml) carefully added to quench the reaction. Excess triethylamine (4 ml) was then added slowly to neutralise the HBr given off and the resultant solution stirred for 30 min after which the mixture was then evaporated in vacuo to dryness. Water (30 ml) was added to the residue and the product extracted using ethyl acetate (4×50 ml). The combined organic extracts were then dried ($Na_2SO_4$) and concentrated in vacuo to dryness to give the crude product. This crude product was dissolved in methanol (10 ml) and acetic acid (0.2 ml) and then heated to reflux. Water (15 ml) was added gradually ensuring the resultant mixture remained at reflux, after which the mixture was allowed to cool to RT and then placed in the fridge overnight. The solid formed was filtered, washed with 40% methanol in water (10 ml) and dichloromethane (3×10 ml) and then dried (vacuum oven, 60° C., 4 h) to yield the title compound (0.17 g, 89%).

NC-m-THPP Physical Data: $\delta_H$ (360 MHz, $CD_3OD$) −4.16 (1H, bs, H-21), 7.22-7.72 (16H, m, $CH_{ar}$), 8.21-8.25 (4H, m, H-8, 12, 13, 17), 8.37 (1H, s, H-3), 8.48 (1H, d, $J_{18,17}$ 4.0 Hz, H-18), 8.62 (1H, bs, H-7); $\lambda_{max}$ ($CH_3OH$): 281 ($\epsilon$ 20 861), 439 ($\epsilon$ 139 386), 538 ($\epsilon$ 6 225), 582 ($\epsilon$ 6 883), 727 ($\epsilon$ 7 673); m/z (+ve FAB, NOBA) 679 (MH$^+$, 15.3%), (Found: MH$^+$ 679.23450. $C_{44}H_{31}N_4O_4$ requires 679.23453).

Example 3

2-Aza-21-carba-2-methyl-5,10,15,20-tetra-(3-hydroxyphenyl)porphyrin (N-Me-NC-m-THPP)

To a solution of NC-m-THPP (40 mg, 0.059 mmol) in dimethylformamide (10 ml) was added methyl iodide (2 ml). The mixture was allowed to stand at RT for 24 h. After removal of the solvent the residue was dissolved in ethyl acetate (20 ml) and extracted with saturated aqueous sodium bicarbonate solution (2×20 ml). The organic layer was dried ($Na_2SO_4$) and evaporated in vacuo. The residue was recrystallised from methanol/water to give N-Me-NC-m-THPP (40 mg, 98%).

N-Me-NC-m-THPP Physical Data: $\lambda_{max}$ ($CH_3OH$) 358, 464, 576, 782.

Alternatively, the steps performed in examples 2 & 3 may be reversed as follows.

Example 4

2-Aza-21-carba-2-methyl-5,10,15,20-tetra-(3-methoxyphenyl)porphyrin (N-Me-NC-m-TMPP)

To a stirred solution of NC-m-TMPP (500 mg, 0.68 mmol) in dichloromethane (50 ml) was added methyl iodide (4.25 ml, 68.1 mmol) and the resultant mixture was stirred at RT overnight. The reaction mixture was then heated under reflux for 1 h after which thin layer chromatography (TLC) analysis (100% dichloromethane) indicated that all the starting material had been consumed. Once cool, the mixture was washed with saturated aqueous sodium bicarbonate solution (2×25 ml) and water (2×25 ml), dried ($Na_2SO_4$) and the solvent removed in vacuo to yield the crude material. This crude product was dissolved in methanol (40 ml) and triethylamine (1 ml) and then heated to reflux for 10 min. The solution was allowed to cool slowly to RT and placed in the fridge for 4 h. The solid formed was filtered, washed with methanol (20 ml) and then dried (vacuum oven, 60° C., 2 h) to yield the title compound (0.42 g, 83%).

N-Me-NC-m-TMPP Physical Data: $\delta_H$ (360 MHz, $CDCl_3$) 1.26 (1H, s, H-21), 3.52 (3H, s, $NCH_3$), 3.96 (6H, s, $OCH_3$), 4.00 (3H, s, $OCH_3$), 4.01 (3H, s, $OCH_3$), 7.15-7.25 (4H, m, $CH_{ar}$), 7.33 (1H, d, $J_{AB}$ 1.4 Hz, H-3), 7.44-7.57 (12H, m, $CH_{ar}$), 7.57-7.61 (2H, m, H-7, 18), 7.84 (2H, m, H-12, 13), 7.93 (1H, d, $J_{17,18}$ 4.6 Hz, H-17), 8.02 (1H, d, $J_{8,7}$ 4.7 Hz, H-8); $\lambda_{max}$ ($CH_2Cl_2$): 274 ($\epsilon$ 24 744), 365 ($\epsilon$ 38 788), 447 ($\epsilon$ 96 105), 582 ($\epsilon$ 8 003), 656 ($\epsilon$ 11 341), 710 ($\epsilon$ 12 856); m/z (+ve FAB, NOBA) 749 (MH$^+$, 100% matrix subtracted), (Found: MH$^+$ 749.31277. $C_{49}H_{41}N_4O_4$ requires 749.31278).

Example 5

2-Aza-21-arba-2-methyl-5,10,15,20-tetra-(3-hydroxyphenyl)porphyrin (N-Me-NC-m-THPP)

N-Me-NC-m-TMPP (200 mg, 0.27 mmol) was dissolved in dry dichloromethane (20 ml) and the solution was cooled to an external temperature of −78° C. A 1.0M solution of boron tribromide in dichloromethane (2.6 ml, 2.6 mmol) was added dropwise and the resultant reaction mixture stirred at −78° C. for 2 h. This was then allowed to warm up slowly to RT with continued stirring overnight. Next day, the mixture was cooled to an external temperature of −10° C. and excess methanol (2 ml) carefully added to quench the reaction. Excess triethylamine (4 ml) was then added slowly to neutralise the HBr given off and the resultant solution stirred for 30 min after which the mixture was then evaporated in vacuo to dryness. The residue was dissolved in methanol (10 ml) and acetic acid (0.2 ml) and then heated to reflux. Water (20 ml) was gradually added ensuring the resultant mixture remained at reflux after which the mixture was allowed to cool to RT and then cooled in the fridge overnight. The solid formed was filtered, washed with water (10 ml) and dichloromethane (2×25 ml) and then dried (vacuum oven, 60° C., 2 h) to yield the title compound (0.18 g, 99%).

N-Me-NC-m-THPP Physical Data: $\delta_H$ (360 MHz, $CD_3OD$) −2.44 (1H, s, H-21), 3.83 (3H, s, $NCH_3$), 7.27-7.31 (2H, m, $CH_{ar}$), 7.40-7.45 (2H, m, $CH_{ar}$), 7.52-7.54 (4H, m, $CH_{ar}$), 7.63-7.67 (2H, m, $CH_{ar}$), 7.75-7.85 (6H, m, $CH_{ar}$), 7.87 (1H, s, H-3), 8.23 (4H, m, H-7, 12, 13, 18), 8.60 (1H, d, $J_{17,18}$ 4.7 Hz, H-17), 8.73 (1H, d, $J_{8,7}$ 4.6 Hz, H-8); $\lambda_{max}$ ($CH_3OH$): 285 ($\epsilon$ 22 806), 371 ($\epsilon$ 31 554), 457 ($\epsilon$ 87 224), 573 ($\epsilon$ 3 873), 636 ($\epsilon$ 3 411), 846 ($\epsilon$ 10 795); m/z (+ve FAB, NOBA) 693 (MH$^+$, trace), (Found: MH$^+$ 693.25018. $C_{45}H_{33}N_4O_4$ requires 693.25018).

Examples of substitution at the 2-N or 21-C are given in Scheme 2 and examples 6-9. The propyl sulfonate derivative is shown as an internal salt, inferred from its property of solubility in both methanol and dichloromethane, unlike the other examples, which are soluble in one or the other only. The deprotection of 21-$NO_2$—NC-m-TMPP and 21-Br-NC-m-TMPP can be performed in a similar manner to that shown for other examples. The syntheses described below outline substitutions of the tetramethoxy derivative followed by demethylation to the tetrahydroxy compound, however it is noted that these steps may be reversed to yield the equivalent desired product.

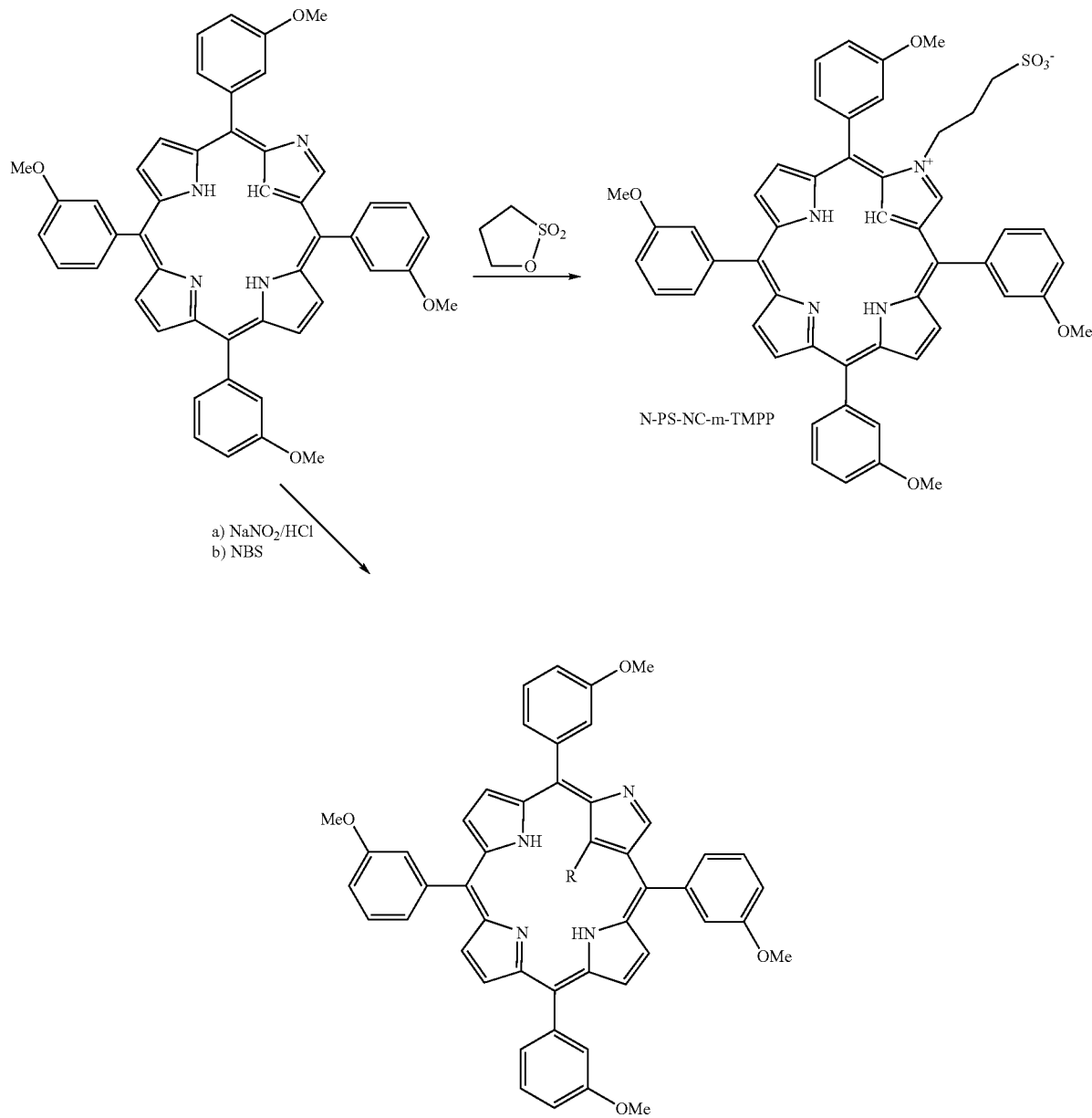

Scheme 2

R = NO₂ = 21-NO₂—NC-m-TMPP
= Br = 21-Br—NC-m-TMPP

Example 6

2-Aza-21-carba-2-propylsulfonate-5,10,15,20tetra-(3-methoxyphenyl)porphyrin (N-PS-NC-m-TMPP)

A mixture of NC-m-TMPP (200 mg, 0.27 mmol), propane sultone (0.96 ml, 10.9 mmol) and triethylamine (0.19 ml, 1.35 mmol) in chloroform (20 ml) was stirred at reflux for 3.5 h after which TLC analysis (100% dichloromethane) indicated that all the starting material had been consumed. The solvent was removed in vacuo and water (40 ml) was then added. A 2.0M solution of aqueous sodium hydroxide (9 ml) was added to give a resultant solution at pH13-14 and this was left stirring at RT overnight. The mixture was then acidified to pH3-4 using acetic acid (3.5 ml) and the resultant solution left stirring at RT for 2 h. The precipitated solid that had formed was filtered, dissolved in methanol (40 ml) and then heated to reflux. Water (50 ml) was gradually added ensuring the resultant mixture remained at reflux after which the mixture was allowed to cool to RT and then cooled in the fridge overnight. The solid formed was filtered, washed with water (20 ml) and then dried (vacuum oven, 60° C., 3 h) to yield the title compound (0.20 g, 83%).

N-PS-NC-m-TMPP Physical Data: $\delta_H$ (360 MHz, CD$_3$OD) −2.40 (1H, bs, H-21), 1.67 (2H, q, J 6.9 Hz, CH$_2$CH$_2$CH$_2$), 2.05 (2H, t, J 6.4 Hz, NCH$_2$), 4.07 (3H, s, OCH$_3$), 4.15 (6H, s, OCH$_3$), 4.24 (2H, t, J 6.9 Hz, CH$_2$SO$_3^-$), 7.41-7.95 (17H, m CH$_{ar}$ and H-3), 8.08 (1H, m, H-8 or 17), 8.10 (1H, d, J 4.7 Hz, H-8 or 17), 8.17 (2H, m, H-12, 13), 8.47 (1H, d, J$_{18,\,17}$ 4.9 Hz, H-18), 8.56 (1H, m, H-7); $\lambda_{max}$ (CH$_3$OH): 296 ($\epsilon$ 22 853), 372 ($\epsilon$ 32 074), 462 ($\epsilon$ 93 000), 573 ($\epsilon$ 4 085), 632 ($\epsilon$ 2 913), 850 ($\epsilon$ 12 077); m/z (+ve FAB, NOBA) 857 (MH$^+$, 10.9%), (Found: MH$^+$ 857.30065. C$_{51}$H$_{45}$N$_4$O$_7$S requires 857.30090).

Example 7

2-Aza-21-arba-2-propylsulfonate-5,10,15,20-tetra-(3-hydroxyphenyl)porphyrin (N-PS-NC-m-THPP)

N-PS-NC-m-TMPP (200 mg, 0.23 mmol) was dissolved in dry dichloromethane (20 ml) and the solution was cooled to an external temperature of −78° C. A 1.0M solution of boron tribromide in dichloromethane (2.1 ml, 2.1 mmol) was added dropwise and the resultant reaction mixture stirred at −78° C. for 2 h. This was then allowed to warm up slowly to RT with continued stirring overnight. Next day, the mixture was cooled to an external temperature of −10° C. and excess methanol (8 ml) carefully added to quench the reaction. Excess triethylamine (10 ml) was then added slowly to neutralise the HBr given off and the resultant solution stirred for 30 min after which the mixture was then evaporated in vacuo to dryness. The residue was dissolved in methanol (24 ml) and acetic acid (0.5 ml) then heated to reflux. Water (56 ml) was gradually added ensuring the resultant mixture remained at reflux, after which the mixture was allowed to cool to RT and then cooled in the fridge overnight. The solid formed was filtered, washed with water (20 ml) and dichloromethane (2×20 ml) and then dried (vacuum oven, 60° C., 2 h) to yield the title compound (0.16 g, 84%).

N-PS-NC-m-THPP Physical Data: $\delta_H$ (360 MHz, DMSO-D$_6$) −2.40 (1H, s, H-21), 1.36 (2H, bs, CH$_2$CH$_2$CH$_2$), 1.57 (2H, bs, NCH$_2$), 4.16 (2H, bs, CH$_2$SO$_3^-$), 7.18-7.72 (16H, m, CH$_{ar}$), 7.96 (1H, s, H-3), 8.05-8.12 (4H, m, H-8, 12, 13, 17), 8.45 (1H, bs, H-18), 8.64 (1H, bs, H-7), 9.80 (2H, bs, OH), 10.10 (2H, bs, OH); $\lambda_{max}$ (CH$_3$OH): 285 ($\epsilon$ 12 518), 371 ($\epsilon$ 17 268), 462 ($\epsilon$ 43 293), 566 ($\epsilon$ 2 838), 794 ($\epsilon$ 4 195), 853 ($\epsilon$ 5 544); m/z (+ve FAB, NOBA) 801 (MH$^+$, 1.2%), (Found: MH$^+$ 801.23834. C$_{47}$H$_{37}$N$_4$O$_7$S requires 801.23830).

Example 8

2-Aza-21-arba-21-nitro-5,10,15,20-tetra-(3-methoxyphenyl)porphyrin (21-NO$_2$-NC-m-TMPP)

A solution of sodium nitrite (2.5 g, 36.2 mmol) and hydrochloric acid (37%, 22.2 ml) in water (227.8 ml) was added to a stirred solution of NC-m-TMPP (250 mg, 0.34 mmol) in dichloromethane (150 ml). The resultant reaction mixture was stirred vigorously at RT for 1 min after which the solution was neutralised by adding 2.0M aqueous sodium hydroxide solution. The organic layer was then separated, washed with water (2×75ml), dried (Na$_2$SO$_4$) and evaporated in vacuo to dryness. The residue collected was dissolved in dichloromethane (25 ml) before being absorbed onto 6 g of basic alumina (activity III) and was added to the top of a column (50 mm) of basic alumina (200 g, activity m) eluting with 100% dichloromethane. The fractions containing the desired product were combined and the solvent removed in vacuo to dryness to yield the title compound (0.24 g, 89%).

21-NO$_2$-NC-m-TMPP Physical Data: $\delta_H$ (360 MHz, CDCl$_3$) −3.45 (1-2H, bs, NH), 3.95-3.98 (6H, m, OCH$_3$), 4.00 (3H, m, OCH$_3$), 4.02 (3H, m, OCH$_3$), 7.33-7.44 (4H, m, CH$_{ar}$), 7.62-7.83 (8H, m, CH$_{ar}$), 8.00-8.05 (4H, m, CH$_{ar}$), 8.13 (1H, s, H-3), 8.60-8.84 (4H, m, H-8, 12, 13, 17), 9.20 (1H, d, J$_{18,\,17}$ 5.0 Hz, H-18), 9.25 (1H, d, J$_{7,\,8}$ 4.9 Hz, H-7); $\lambda_{max}$ (CH$_2$Cl$_2$): 280 ($\epsilon$ 23 591), 368 ($\epsilon$ 39 387), 472 ($\epsilon$ 166 850), 646 ($\epsilon$ 13 657), 698 ($\epsilon$ 13 040); m/z (+ve FAB, NOBA) 780 (MH$^+$, 7.9%), (Found: MH$^+$ 780.28218. C$_{48}$H$_{38}$N$_5$O$_6$ requires 780.28221).

Example 9

2-Aza-21bromo-21-carba-5,10,15,20-tetra-(3-methoxyphenyl)porphyrin (21-Br-NC-m-TMPP)

A solution of NC-m-TMPP (50 mg, 69 µmol) and N-bromosuccinimide (15 mg, 83 µmol) in dichloromethane (5 ml) was stirred for 5 min at RT after which TLC (100% dichloromethane) indicated that all the starting material had been consumed. The product was then pre-absorbed onto 5 g of basic alumina (activity III) and was added to the top of a column (20 mm) of basic alumina (30 g, activity III) eluting with 100% dichloromethane. Fractions were combined and the solvent evaporated in vacuo to give the title compound (24 mg, 43.3%).

21-Br-NC-m-TMPP Physical Data: $\delta_H$ (200 MHz, CDCl$_3$) 3.97-4.03 (6H, m, OCH$_3$), 4.08 (3H, s, OCH$_3$), 4.12 (3H, s, OCH$_3$), 7.28-8.07 (17H, m, CH$_{ar}$ and H-3), 8.55-8.62 (4H, m, H-8, 12, 13, 17), 8.96 (1H, d, J$_{18,\,17}$ 4.5 Hz, H-18), 9.06 (1H, d, J$_{7,\,8}$ 4.9 Hz, H-7); m/z (+ve FAB, NOBA) 815 (MH$^+$, trace), 735 (MH$^+$-Br, trace), 613 (MH$^+$-Br-(4× OCH$_3$), 1.3%), 460 (MH$^+$-Br-(4×OCH$_3$)-2Ph, 8.7%).

Further N-Substituted N-confused Porphyrins

In the discussion earlier in this patent, it is stated that the external nitrogen is a convenient attachment point for functionalisation. Such groups that can be attached may be designed to promote water solubility in the product, which is a desired attribute in a pharmaceutical, and possibly increase the intensity of the lowest energy Q band. The synthesis of some of these compounds is given in Scheme 3. The initial substitution reaction may be aided by the addition of bases such as Et$_3$N, DIPEA or DMAP. Water solubilising groups such as m-PEG, carbohydrates or amino acid residues can then be coupled to the derivative obtained.

Scheme 3

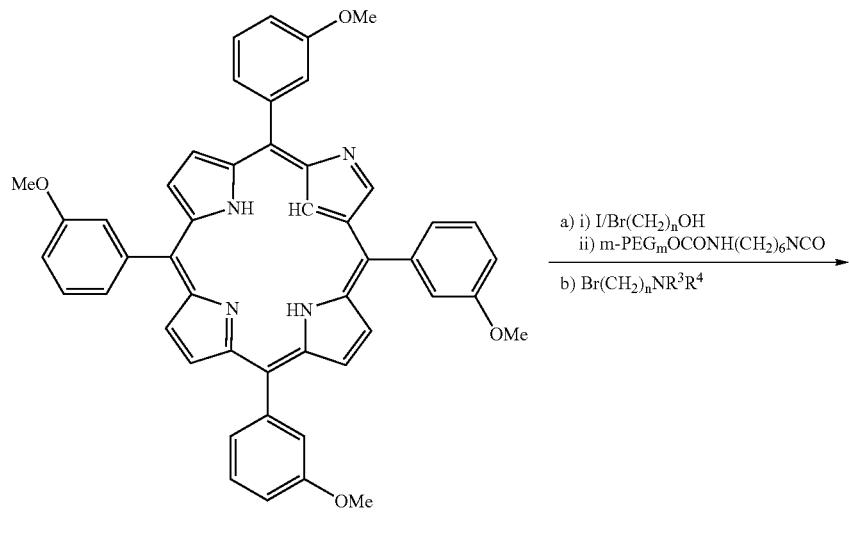

a) i) I/Br(CH$_2$)$_n$OH
   ii) m-PEG$_m$OCONH(CH$_2$)$_6$NCO
b) Br(CH$_2$)$_n$NR$^3$R$^4$

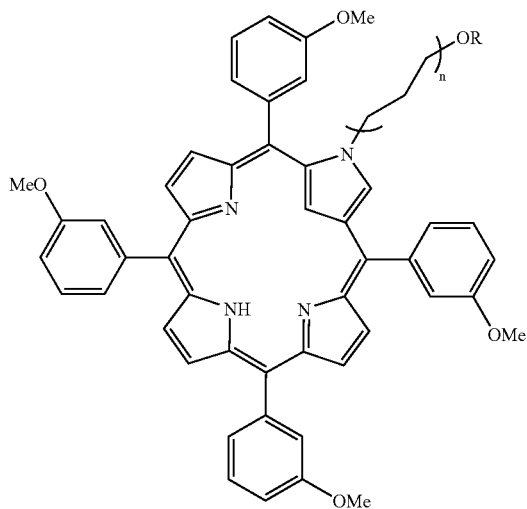

R = NR$^3$R$^4$
  = CONH(CH$_2$)$_6$NHCO$_2$-m-PEG$_m$

Synthesis of N-confused Chlorins and Bacteriochlorins of Types IIIA-D and VA-F from N-confused Porphyrins of Type IIA and N-confused Chlorins and Bacteriochlorins of Types IVA-D and VIA-F from N-confused Porphyrins of Type IIB Porphyrins with imidazole substituents are easily reduced to chlorins and bacteriochlorins via hydrogen transfer catalysis. We expected that electron-withdrawing substituents would render the porphyrin macrocycle more susceptible to hydrogen transfer. In searching for other systems on which to test this hypothesis, we uncovered the work by Lindsey on N-confused porphyrins. We expected that the external nitrogen should similarly make the macrocycle more susceptible to hydrogen transfer envisaging that hydrogen will add specifically across the external 2,3 —N=C— bond in the macrocycle.

Reduction of the N-confused porphyrins via hydrogen transfer catalysis, using 10% Pd on charcoal or Pd black and formic acid as hydrogen transfer reagent, indicated that with N-confused porphyrins, 10% Pd on charcoal achieves reduction to a chlorin-like species with a broad intense band at 686 nm and an intensity almost 50% that of the B band at 435 nm. This is in comparison with m-THPC which has a Q/B band ratio of 15-20%. Further work has shown that reduction to the N-confused chlorin occurs with $NaCNBH_3$ in the presence of acid.

Reduction of the N-confused porphyrins can be performed by using catalytic hydrogen transfer or with agents that supply hydride ions, $H^-$, such as alkali metal boron and aluminium hydrides. These preferentially reduce the 2,3 —N═C— bond to produce an N-confused chlorin without further reduction to give an N-confused bacteriochlorin (See Scheme 4). The addition of acid to reactions with the above named reagents aids in polarization of the 2,3 —N═C— bond and allows hydride ion attack to occur more readily.

From the literature, (Whitlock et al. J. Am. Chem. Soc. 1969, 91, 7485), it is indicated that reduction of a porphyrin with diimide (used in the production of the known PDT agent, m-THPC) will proceed by the initial reduction of a peripheral ring —C═C— bond. If the 12,13 bond of the N-confused porphyrin is reduced preferentially by this method, then further reduction to an N-confused bacteriochlorin is slow as the opposing ring contains the —C═N— bond, which would not be reduced by this reagent. The N-confused chlorin will therefore be the predominant product.

In the reduction of m-THPP, the bacteriochlorin is produced as an intermediate, which can then be oxidised to the chlorin. The N-confused bacteriochlorin will not be formed in this way as we are proposing a stepwise synthesis. Thus only the sequential hydride or hydrogen transfer reaction followed by diimide reduction or vice versa will form the N-confused 2,3-12,13 bacteriochlorin (see Scheme 4).

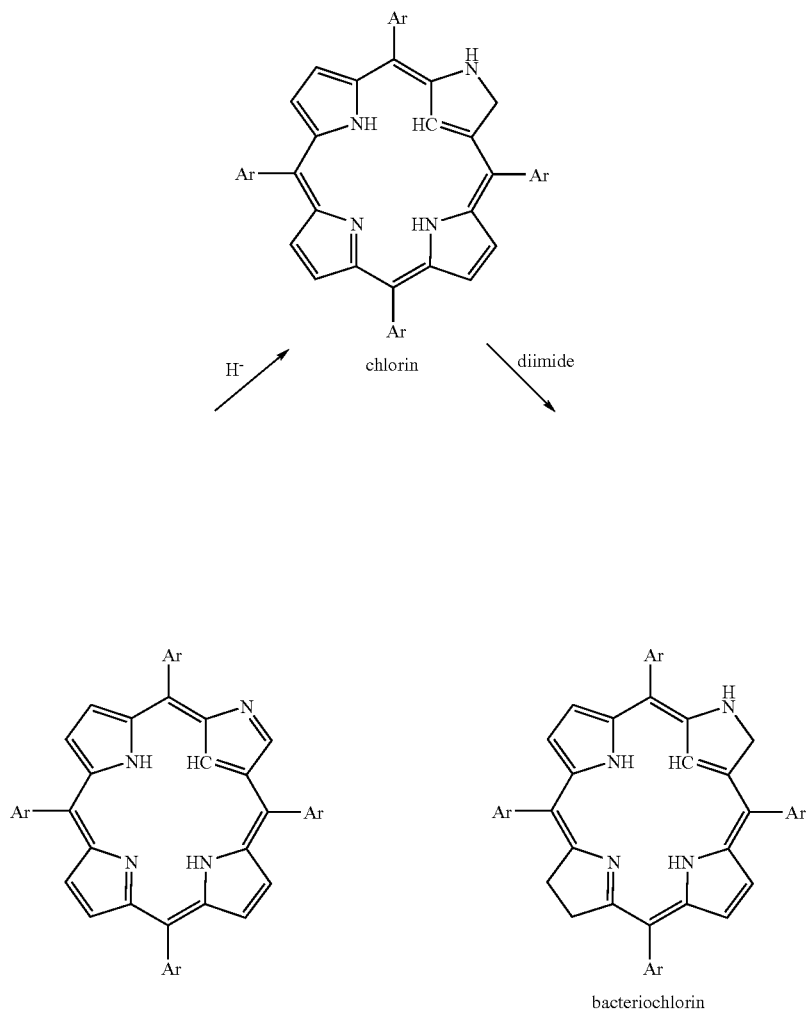

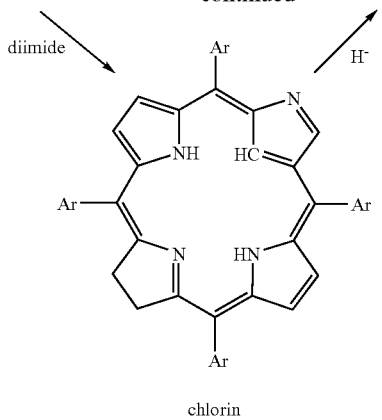

chlorin

Example 10

2-Aza-21-arba-5,10,15,20-tetra-(3-methoxyphenyl) dihydroporphyrin (NC-m-TMPC)

A mixture of NC-m-TMPP (100 mg, 0.14 mmol) and hydrochloric acid (37%, 0.57 ml, 6.87 mmol) in 15:1 tetrahydrofuran/methanol (10 ml) was added to sodium cyanoborohydride (14.4 mg, 0.23 mmol) with vigorous stirring under an $N_2$ blanket. The resultant reaction mixture (pH2-6) was then left for 30 min after which TLC analysis (100% dichloromethane) indicated that all the starting material had been consumed. The mixture was then neutralised with 2.0M aqueous sodium hydroxide solution and the product extracted using dichloromethane (2×50 ml). The combined organic extracts were washed with water (40 ml), dried ($Na_2SO_4$) and concentrated in vacuo to dryness. The residue collected was then dissolved in 75% dichloromethane in hexane (3 ml) and added to the top of a column (20 mm) of basic alumina (35 g, activity III) eluting with 75% dichloromethane in hexane. Fractions containing the new product were combined and the solvent removed under vacuo to give the title compound (17.9 mg, 17.7%).

NC-m-TMPC Physical Data: $\lambda_{max}$ ($CH_2Cl_2$): 282 ($\epsilon$ 18 360), 309 ($\epsilon$ 20 567), 421 ($\epsilon$ 47 183), 698 ($\epsilon$ 24 329); m/z (+ve FAB, NOBA) 737 ($MH^+$, 42.4% or 100% when matrix subtracted).

N-confused chlorins and bacteriochlorins of types IVA-D and VIA-F can also be synthesised from N-confused porphyrins of Type IIIA by a two step process of reduction followed by substitution of the external nitrogen with the appropriate R group (See Scheme 5). This provides an alternative route to the desired compounds.

Scheme 5

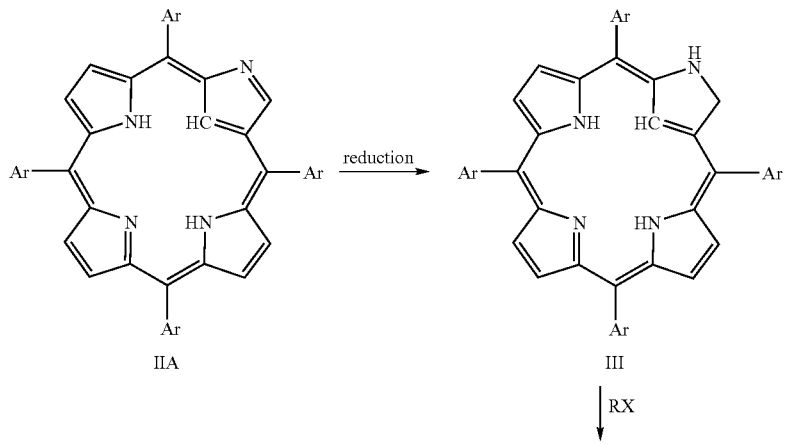

-continued

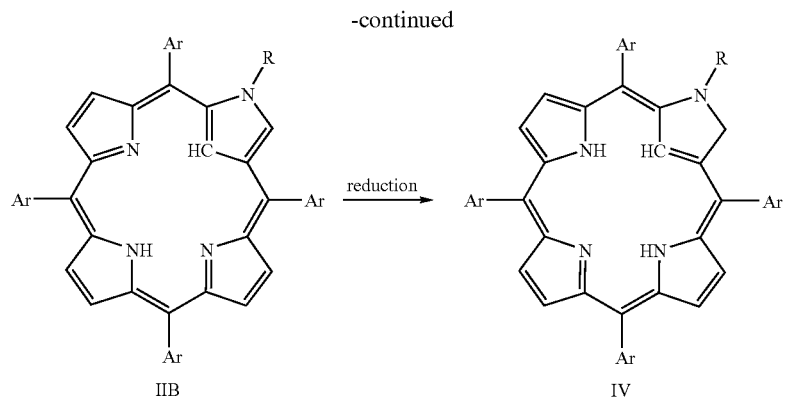

IIB → reduction → IV

BIOLOGY

The biological efficacy of one of the N-confused porphyrins was tested as detailed below.

Experimental

N-Me-NC-m-THPP was dissolved in dilution vehicle (polyethylene glycol 400:ethanol:water 3:2:5 v:v:v) to produce a stock solution of 0.72 mgml$^{-1}$.

Adult female Balb/c mice bearing the syngeneic colo26 tumour implanted subcutaneously were treated with N-Me-NC-m-THPP at a dose of 2.6 μmol kg$^{-1}$ (1.8 mg kg$^{-1}$) by injection of the stock solution at a volume of 2.5 μlg$^{-1}$ live weight into the tail vein. Twenty-four hours after injection of the photosensitiser, an area of 1.5 cm diameter surrounding the tumour was irradiated with broad-spectrum white light derived from a high-pressure xenon lamp (Applied Photo Physics clinical photo-irradiator model UV90, serial 020). The power density at the skin surface was 713 mWcm$^{-2}$ and irradiation was applied for 70 s to give a total light dose of just under 50 Jcm$^{-2}$. The tumours were assessed 24 h after irradiation, when the animals were sacrificed and the irradiation site examined and the depth of necrosis measured. Results are shown in table 1 below.

In a separate group of mice, the normal tissue damage was assessed by irradiating one ear with 40 Jcm$^{-2}$ of broad spectrum white light delivered using a fibre bundle from the xenon light source. The incident power at the ear surface was 638 mWcm$^{-2}$ and light was applied for 63 s. Animal ears were irradiated with light 24 h after administration of N-Me-NC-m-THPP. The opposing ear served as a control. The response was assessed twenty-four hours after irradiation by measuring the ear thickness at three sites on the upper third of the ear using a fixed-force micrometer with a vernier-interpolated resolution of 2 μm and an accuracy of 10 μm (Neill instruments).

No adverse effects to the animals were noted on injection of N-Me-NC-m-THPP and no subsequent toxic reactions were noted. The animals were held in subdued lighting conditions (ambient light ranged from 10 to 300 lux) and no phototoxicity was noted. There were no notable responses on irradiation, although some animals gave signs of slight discomfort during light delivery. When examined 24 h after irradiation, all of the treated tumours showed extensive signs of photonecrosis. In addition, in two of the animals an area of mildly oedematous skin was observed corresponding to the irradiated area In all cases, tumour necrosis extended the full thickness of the tumour. The depths of necroses noted were 5.5, 2.5 and 7.0 mm.

On measurement of the ear thickness, no difference was found between the irradiated and control ears in the N-Me-NC-m-THPP treated animals. The mean difference (irradiated-control) was −2 μm with a standard error of 5 μm. In the case of animals treated with m THPC at 0.88 μMkg$^{-1}$ irradiated at the same light dose 24 h after drug injection, the mean difference in ear thickness (irradiated-control) was 41 μm.

TABLE 1

| Compound | Dose (μmol/kg) | |
|---|---|---|
| | | Tumour necrosis (mm; mean ± SD) |
| N—Me—NC-m-THPP | 2.6 | 5.0 ± 2.3 (n = 3) |
| | | Ear Swelling (irradiated − control; μm) |
| N—Me—NC-m-THPP | 2.6 | −2 (±5 Standard Error) |
| m-THPC | 0.88 | 41 |

The results on tumour necrosis show effective photodynamic therapeutic (PDT) activity for N-Me-NC-m-THPP using broad spectrum white light. An improvement in the potency of this effect is anticipated with the use of light selective to the Q band of the N-Me-NC-m-THPP. In comparison to literature reported data (Berenbaum et al. Lasers in Medical Science 1993, 8, 235-243) on the activity of m-THPP in this model, which shows tumour necrosis of 0.14 mm at an m-THPP dose of 1.61 μmol/kg and using light at 652 nm, this PDT activity of N-Me-NC-m-THPP is very promising. Results on photosensitivity, tested by ear swelling, suggest that N-Me-NC-m-THPP shows little or no cutaneous photosensitivity compared to m-THPC. This signifies a potentially important therapeutic advantage for N-Me-NC-m-THPP and other N-confused porphyrins, chlorins and bacteriochlorins of the present invention.

We claim:

1. N-confused tetrahydroxyphenyl and tetra-alkoxyphenyl prophyrins represented as:

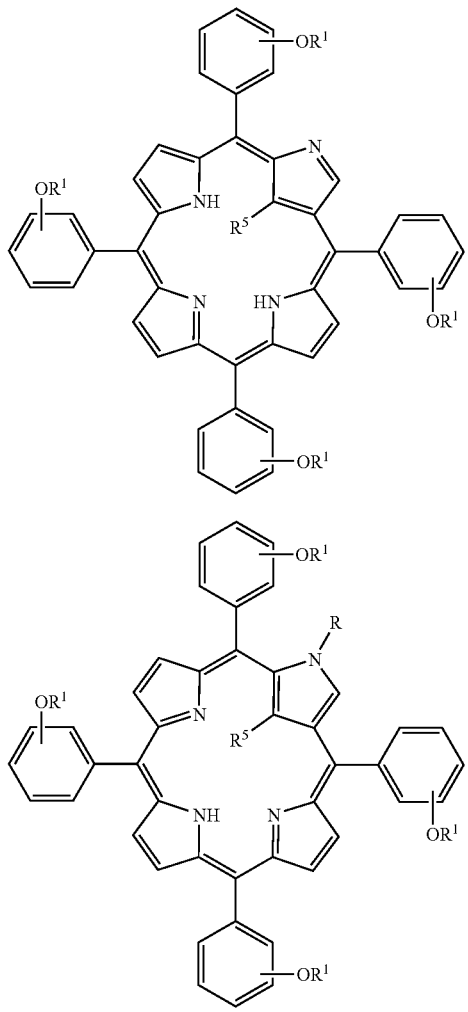

and the corresponding chlorins (dihydroporphyrins) and bacteriochlorins (tetrahydroporphyrins), including tautomers in all cases; and their metallates and salts, including internal salts:

—$OR^1$ standing for a hydroxy group ($R^1$=hydrogen) or an alkoxy group where $R^1$ is a branched or unbranched alkyl group containing from 1 to 4 carbon atoms, and where $OR^1$ may be at any position on the phenyl ring and there may be zero, one, two or three groups per phenyl ring provided at least one of the rings is substituted and —R standing for hydrogen, when IIB and IIA represent the same molecule, or R=X, a branched or unbranched alkyl group of 1 to 6 carbon atoms, or an aralkyl group the alkyl chain of which contains 1 to 3 carbon atoms, or alternatively R=XY where X is as defined above and Y consists of 1 to 3 substituents which are attached to any of the carbons in X and may be linked, and which are selected from:

=—$SO_3H$, $CO_2H$ and their C1 to C12 esters and amides;

=—OH or $OR^2$ where $R^2$=a polyhydroxylated alkyl chain from 1 to 20 carbon atoms;

=—$NR^3R^4$ where $R^3$, $R^4$ are the same or different and may be hydrogen or an alkyl group of 1 to 12 carbon atoms or a polyhydroxylated alkyl chain or folic acid residue;

=Z-P where P is an end-capped polyalkylene glycol group of molecular weight of 2,000 to 100,000 and Z is a linker group to attach P;

$R^5$=hydrogen, a halogen or a nitro group.

2. The compound 2-Aza-21-carba-5,10,15,20-tetra(3-methoxyphenyl)prophyrin (NC-m-TMPP), 2-Aza-21-carba-5,10,15,20-tetra(3-hydroxyphenyl)prophyrin (NC-m-THPP), 2-Aza-21-carba-2-methyl-5,10,15,20-tetra-(3-hydroxyphenyl)prophyrin (N-Me-NC-m-THPP), 2-Aza-21-carba-2-methyl-5,10,15,20-tetra-(3-methoxyphenyl) prophyrin (N-Me-NC-m-TMPP), 2-Aza-21-carba-2-methyl-5,10,15,20-tetra-(3-hydroxyphenyl)prophyrin (N-Me-NC-m-THPP), 2-Aza-21-carba-2-propylsulfonate-5,10,15,20-tetra-(3-methoxyphenyl)prophyrin (N-PS-NC-m-TMPP), 2-Aza-21-carba-2-propylsulfonate-5,10,15,20-tetra-(3-hydroxyphenyl)prophyrin (N-PS-NC -m-THPP), 2-Aza-21-carba-21-nitro-5,10,15,20-tetra-(3-methoxyphenyl)prophyrin (21-$NO_2$-NC-m-TMPP), 2-Aza-21-bromo-21-carba-5,10,15,20-tetra-(3-methoxyphenyl)prophyrin (21-Br-NC-m-TMPP), or 2-Aza-21-carba-5,10,15,20-tetra-(3-methoxyphenyl)dihydroporphyrin (NC-m-TMPC).

3. A compound according to claim 1 where chain $OR^1$ is attached at the meta position of the phenyl ring.

4. A compound according to claim 1 where Y is a carbohydrate or a folic acid residue.

5. A compound according to claim 1 where P is an end-capped polyethylene glycol group.

6. A compound according to claim 1 where P is an end-capped polyalkylene group of molecular weight of 5,000 to 40,000.

7. A compound according to claim 1 where P is an end-capped polyalkylene group of molecular weight of 10,000 to 20,000.

8. A compound according to claim 1 where Z is a —O(C=O)NH($CH_2$)$_6$NH(CH=O)O— group.

* * * * *

UNITED STATES PATENT AND TRADEMARK OFFICE
CERTIFICATE OF CORRECTION

PATENT NO. : 7,319,147 B2  Page 1 of 1
APPLICATION NO. : 10/363909
DATED : January 15, 2008
INVENTOR(S) : Manku et al.

It is certified that error appears in the above-identified patent and that said Letters Patent is hereby corrected as shown below:

Title page of the patent, left hand column "(75) Inventors", please insert --Lionel Milgrom, London (GB)--.

Signed and Sealed this

Twenty-ninth Day of June, 2010

David J. Kappos
*Director of the United States Patent and Trademark Office*